United States Patent [19]

Wehner et al.

[11] 4,080,468

[45] Mar. 21, 1978

[54] METHOD OF COMBATING INSECT PESTS IN PLANT CULTURES EMPLOYING DIMETHYLTIN-DIACETATE

[75] Inventors: Hermann Wolfgang Wehner, Zwingenberg, Germany; Jozef Drabek, Allschwil, Switzerland

[73] Assignee: Ciba-Geigy Corporation, Ardsley, N.Y.

[21] Appl. No.: 694,006

[22] Filed: Jun. 8, 1976

[30] Foreign Application Priority Data

Jun. 12, 1975 Switzerland .......................... 7615/75
May 11, 1976 Switzerland .......................... 5889/76

[51] Int. Cl.$^2$ .................... A01N 9/00; A01N 9/24
[52] U.S. Cl. ..................................................... 424/288
[58] Field of Search ........................................ 424/288

[56] References Cited

FOREIGN PATENT DOCUMENTS 797,073  6/1958  United Kingdom ................. 424/288
760,056  10/1956  United Kingdom ................. 424/288

*Primary Examiner*—Allen J. Robinson
*Attorney, Agent, or Firm*—Frederick H. Rabin

[57] ABSTRACT

The invention relates to a method of combating insect pests in plant cultures employing dimethyltin-diacetate.

4 Claims, No Drawings

METHOD OF COMBATING INSECT PESTS IN PLANT CULTURES EMPLOYING DIMETHYLTIN-DIACETATE

The present invention relates to the use of dimethyltin diacetate for combating insects which cause damage to plants and provides pesticidal compositions which contain this compound as active component.

It has long been known to use organo-tin compounds for combating a variety of parasites, for example bacteria, fungi, insects, representatives of the order Acarina, harmful rodents, and to use them in the field of material protection. For example, U.S. Pat. No. 3,544,608 and Canadian Pat. No. 905,286 describe a large number of organo-tin compounds, including dimethyltin iodide, diethyltin dinitrite, dimethyltin dicyanate, bis(tributyl-tin)maleate, dimethyltin oxide and dimethyltinbis-isooctyl-mercapto-acetate, as compositions for combating insects, for example mosquitoes and ectoparasites of domestic animals and productive livestock.

Up to the present time, many attempts have been made to combat insects and other pests in plant cultures using such organo-tin compounds with pesticidal action. However, most of these compounds are highly to very highly phytotoxic and are therefore not suitable for combating plant pests.

The surprising discovery has now been made that the dimethyltin diacetate used according to the present invention has a very advantageous pesticidal activity against eating insects which cause damage to plants, in particular insects of the order *Lepidoptera* and *Colleoptera*, but — in contrast to other organo-tin compounds — has no, or only a very low, phytotoxicity. Since the tin compounds closest to dimethyltin diacetate, for example dimethyltin diformiate, do not possess any striking insecticidal properties, it is particularly surprising that the tin salt used according to this invention does have the above described useful properties.

In comparison with other organo-tin pesticidal compositions, for example the readily volatile trialkyl tin halides described in German Offenlegungsschrift No. 1,139,691, dimethyltin diacetate is also very stable and in addition has the advantage of being markedly less toxic to warm-blooded animals, a feature which is of especial importance for an insecticide at the present time in view of increasing concern for environmental protection.

The compound used according to the present invention itself, that is to say, dimethyltin diacetate, is already known, as are also methods of obtaining it; cf. for example "Journal of Organometallic Chemistry" 10 (1967), 247–256. However, its particular properties in respect of phytotoxicity and insecticidal activity were hitherto unknown and are described herein for the first time.

Accordingly, the present invention relates to the use of dimethyltin diacetate for combating insects which cause damage to plants in plant cultures, particularly in cultures of useful plants, and above all for combating harmful eating insects in cotton plantations (for example *Heliothis virescens* and *Spodoptera littoralis*) and in vegetable crops (for example *Leptinotarsa decemlineata*). When used against individual insect species. for example *Heliothis virescens*, the compound of this invention is observed to have both an ovicidal and larvicidal action as well as an action against adults.

The rates of application must be adapted to the circumstances (nature of the useful plant, climate, time of application etc.), and are advantageously between 100g and 1000g, normally between 250g and 750g, of dimethyltin acetate per hectare.

The insecticidal or acaricidal action can be substantially broadened and adapted to give circumstances by addition of other insecticides. Examples of suitable additives are: organic phosphorus compounds, nitrophenols and derivatives thereof, formamidines, ureas, pyethroids, carbamates, and/or chlorinated hydrocarbons.

The dimethyltin diacetate can be used as pure active substance or together with suitable carriers and/or additives. Suitable carriers and additives can be solid or liquid and correspond to the substances conventionally used in formulation technology, for example natural or regenerated substances, solvents, dispersants, wetting agents, stickers, thickeners, binders and/or fertilisers.

For application, the dimethyltin diacetate can be processed to dusts, emulsion concentrates, granules, dispersions, sprays, to solutions, or suspensions, in the conventional formulation which is commonly employed in application technology.

The compositions according to the invention are manufactured in known manner by intimately mixing and/or grinding the active substance with the suitable carriers, with or without the addition of dispersants or solvents which are inert to the active substances.

The dimethyltin diacetate can take, and be used in, the following forms:

Solid forms
  Dusts, tracking agents, granules, coated granules, impregnated granules and homogeneous granules.
Liquid forms
  a. active substances which are dispersible in water: wettable powders, pastes, emulsions;
  b. solutions.

The content of active substance in the above described compositions is between 0.1% to 95%, in which connection it must be mentioned that, when the compositions are applied from an aeroplane or by means of other appropriate devices, higher concentrations can also be used.

The active substances of the formula I can, for example, be formulated as follows:

Dusts

The following substances are used to manufacture (a) a 5% and (b) a 2% dust:

(a)

5 parts of dimethyltin diacetate,
95 parts of talcum;

(b)

2 parts of dimethyltin diacetate,
1 part of highly dispersed silicic acid,
97 parts of talcum.

The active substance is mixed with the carriers and ground.

Granulate

The following substances are used to produce a 5% granulate:

5 parts of dimethyltin diacetate,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder

The following constituents are used for the preparation of (a) a 40%, (b) and (c) a 25%, and (d) a 10% wettable powder:

(a)

40 parts of dimethyltin diacetate,
5 parts of sodium lignin sulphonate,
1 part of sodium dibutyl-naphthalene sulphonate,
54 parts of silicic acid.

(b)

25 parts of dimethyltin diacetate,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

(c)

25 parts of dimethyltin diacetate,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of kieselgur,
46 parts of kaolin.

(d)

10 parts of dimethyltin diacetate,
3 parts of a mixture of the sodium salts of saturated fatty alcohol sulphates,
5 parts of naphthalenesulphonic acid/formaldehye condensate,
82 parts of kaolin.

The active substance is intimately mixed, in suitable mixers, with the additives, and the mixture is then ground in appropriate mills and rollers. Wettable powders are obtained which can be diluted with water to give suspensions of the desired concentration.

Emulsifiable concentrates

The following substances are used to produce (a) a 10%, (b) a 25% and (c) a 50% emulsifiable concentrate:

(a)

10 parts of dimethyltin diacetate,
3.4 parts of epoxidised vegetable oil,
3.4 parts of a combination emulsifier consisting of fatty alcohol polyglycol ether and alkyl aryl sulphonate calcium salt,
40 parts of dimethyl formamide,
43.2 parts of xylene.

(b)

25 parts of dimethyltin diacetate,
2.5 parts of epoxidised vegetable oil,
10 parts of an alkylarylsulphonate/fatty alcohol-glycol ether mixture,
5 parts of dimethylformamide,
57.5 parts of xylene.

(c)

50 parts of dimethyltin diacetate,
4.2 parts of trobutylphenol polyglycol ether,
5.8 parts of calcium dodecylbenzenesulphonate,
20 parts of cyclohexanone,
20 parts of xylene.

From these concentrates it is possible to produce, by dilution with water, emulsions of the desired concentration.

Spray

The following constituents are used to prepare a 5% spray:

5 parts of dimethyltin diacetate,
1 part of epichlorohydrin,
94 parts of benzene (boiling limits 160° C–190° C).

EXAMPLE 1

Lasting insecticidal stomach poison action against *Spodoptera littoralis, Heliothis virescens* and *Leptinotarsa decemlineata*

Cotton and potato plants were sprayed with a 0.05% aqueous emulsion of active substance of dimethyltin diacetate (compound A).

After the spray coating had dried, the cotton plants were populated with *Spodoptera littoralis* and *Heliothis virescens* larvae ($L_3$ stage) and the potato plants with *Leptinotarsa decemlineata* larvae ($L_3$). The percentage mortality was evaluated after 48 hours. Where the mortality was 100% after this interval of time, the plants were populated with fresh larvae and a second mortality count was made after a further 48 hours. If 100% mortality was again attained, then the test was repeated 4 days later (i.e. 8 days after the start of the test).

The comparison compounds used in this test were:

Compound B 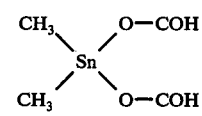

Compound C 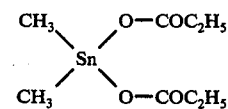

Compound D 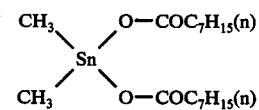

The test carried out at 24° C and 60% relative humidity.

RESULTS
Percentage mortality after 48 hours

| COMPOUNDS | SPODOPTERA LITTORALIS | | | HELIOTHIS VIRESCENS | | | LEPTINOTARSA DECEMLINEATA | | |
|---|---|---|---|---|---|---|---|---|---|
| | X | Y | Z | X | Y | Z | X | Y | Z |
| A | 100% | 100% | 100% | 100% | 100% | 100 | 100% | 100% | 30% |
| B | 20% | — | — | 10% | — | — | 0% | — | — |
| C | 0% | — | — | 0% | — | — | 0% | — | — |
| D | 0% | — | — | 0% | — | — | 0% | — | — |

X = immediate infestation of the plants
Y = infestation of the plants after 2 days
Z = infestation of the plants after 8 days

EXAMPLE 2

Cotton fields heavily infested with eggs of the insect species, Heliothis virescens, were examined and the loci of the individual eggs were marked. The fields were then sprayed with 120 l/ha of an aqueous active substance emulsion (amount of active substance: 500 g/ha). The loci of the eggs were examined after 6 days and a count was made of the eggs that did not hatch out.

The dimethyltin diacetate used according to this invention exhibits a positive ovicidal action in the above test.

What is claimed is:

1. A method of combating insect pests in a plant culture which comprises applying to the said pests an insecticidally effective amount of dimethyltin-diacetate.

2. The method according to claim 1 wherein the plant culture is a growing agricultural crop.

3. The method according to claim 2 wherein the crop is a cotton or vegetable crop.

4. The method according to claim 2 wherein the insect pests are of the order *Lepidoptera* or *Colleoptera*.